(12) United States Patent
Banister et al.

(10) Patent No.: US 6,303,106 B1
(45) Date of Patent: Oct. 16, 2001

(54) ALLOMELANIN PRODUCTION

(75) Inventors: Nigel E. Banister, London; Peter S. J. Cheetham, Tunbridge Wells, both of (GB)

(73) Assignee: Zylepsis Limited (GB)

( * ) Notice: Subject to any disclaimer, the term of this patent is extended or adjusted under 35 U.S.C. 154(b) by 0 days.

(21) Appl. No.: 09/077,912

(22) PCT Filed: Dec. 9, 1996

(86) PCT No.: PCT/GB96/03015

§ 371 Date: Sep. 25, 1998

§ 102(e) Date: Sep. 25, 1998

(87) PCT Pub. No.: WO97/20944

PCT Pub. Date: Jun. 12, 1997

(30) Foreign Application Priority Data

Dec. 7, 1995 (GB) .................................... 9524997
Dec. 13, 1995 (GB) .................................... 9525428

(51) Int. Cl.$^7$ .................................................. A61K 7/135
(52) U.S. Cl. ........................ 424/62; 424/401; 424/450; 514/568; 514/569; 514/944
(58) Field of Search ........................ 424/62, 401, 450; 514/568, 569, 944

(56) References Cited

U.S. PATENT DOCUMENTS

| | | | |
|---|---|---|---|
| 4,515,773 | * | 5/1985 | Herlihy et al. . |
| 5,164,185 | * | 11/1992 | Charpin et al. ..................... 424/401 |
| 5,218,079 | * | 6/1993 | Pawelek et al. ..................... 528/206 |
| 5,227,459 | | 7/1993 | Pawelek et al. ..................... 528/206 |
| 5,244,497 | | 9/1993 | Junino et al. ....................... 106/498 |
| 5,286,979 | * | 2/1994 | Berliner et al. ................... 250/515.1 |
| 5,395,624 | * | 3/1995 | Li et al. ............................. 424/450 |
| 5,445,816 | * | 8/1995 | Li et al. ............................. 424/62 |
| 5,529,909 | * | 6/1996 | Della-Cioppa et al. ........... 435/69.7 |
| 5,547,658 | * | 8/1996 | Hansenne et al. ................... 424/59 |
| 5,618,519 | * | 4/1997 | Pawelek et al. ..................... 424/59 |
| 5,631,151 | * | 5/1997 | Della-Cioppa et al. ........... 435/133 |
| 5,744,125 | * | 4/1998 | Pawelek et al. ..................... 424/59 |

FOREIGN PATENT DOCUMENTS

| | | |
|---|---|---|
| 386 680 | * 9/1990 | (EP) . |
| 01013017 | * 1/1989 | (JP) . |
| 09151130 | * 6/1997 | (JP) . |
| WO 92/00373 | 1/1992 | (WO) . |
| 94/00097 | * 1/1994 | (WO) . |
| WO 95/33706 | 12/1995 | (WO) . |
| WO 96/39859 | 12/1996 | (WO) . |

OTHER PUBLICATIONS

Miyazaki et al. "Inhibitory effects of melanogenic inhibitors on dendricity of cultured B16 mouse melanoma cells" Nippon Koshohin Kagakkaishi, vol. 22(3): 182–186, 1998.*

Ellis, B. E., and Amrhein, N., "The 'Nih–Shift' During Aromatic Orthohydroxylation In Higher Plants", Phytochemistry, 1971, vol. 10, pp. 3069 to 3072.

Gestetner, B. and Conn, E. E., "The 2–Hydroxylation of Trans–Cinnamic Acid by Chloroplasts from Melilotus alba Desr", Archives of Biochemistry and Biophysics 163, 617–624 (1974).

Brand–Williams, W., Cuvelier, M. E. and Berset, C., "Use of a Free Radical Method to Evaluate Antioxidant Activity", Lebensm.–Wiss. u.—Technol., 28, 25–30 (1995).

* cited by examiner

*Primary Examiner*—Ralph Gitomer
*Assistant Examiner*—Devesh Khare

(57) ABSTRACT

A method of producing a melanin comprises oxidizing a phenolic compound at one or more hydroxyl groups thereof, wherein the phenolic compound is selected from 5-hydroxyindole and derivatives thereof and compounds of formula (1) and the oxidation is provided by biotransformation in the presence of an oxidoreductase enzyme, the compound of formula (1),

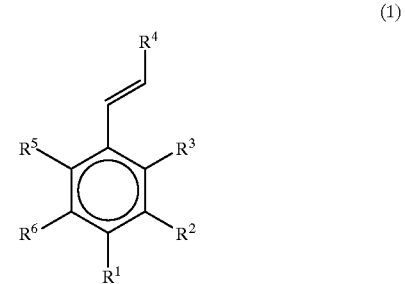

(1)

wherein $R^1$ is H or OH; $R^2$ is H, OH orOCH$_3$; $R^3$ is H or OH at least one of $R^1$ and $R^3$ being OH; $R^4$ is selected from H , R, —COOX and $R^7$—COOX, wherein R is an optionally substituted saturated or unsaturated alkyl group having from 1 to 12 carbon atoms, $R^7$ is an optionally substituted saturated or unsaturated alkylene group having from 1 to 12 carbon atoms and X is selected from H and aliphatic and aromatic ester forming groups; and $R^5$ and $R^6$ is each independently selected from H, OH, NH$_2$, OCH$_3$, CH$_3$, SH, NHCO$_2$, NHCH$_3$, COOH and saturated or unsaturated alkyl groups having up to 8 carbon atoms.

32 Claims, No Drawings

ALLOMELANIN PRODUCTION

Priority is claimed from GB 9524997.5 filed Dec. 7, 1995, GB 9525428.0 filed Dec. 13, 1995, and PCT/GB96/03015 filed Dec. 9, 1996.

The present invention relates to melanins.

Melanins comprise a family of pigments which are naturally present in the hair, eyes and skin of humans and animals. They command high levels of interest for a variety of reasons. Melanins are polymers derived from phenolic monomers. These highly coloured materials lack well defined chemical and physical characterisation but, nonetheless, generate considerable commercial interest for their social, cosmetic and protective implications.

At present natural melanins are extracted from biological sources such as hair and squid ink. There also exist methods of industrially synthesising these materials using oxidative enzymes or genetic manipulation. For example, melanins obtained from the amino acids tyrosine and DOPA are produced in this way. Such materials have been used in the prior art to produce hair colourings, as antioxidants in skin creams and in other cosmetic formulations.

There are significant problems associated with melanins produced as in the prior art. The dark pigmentation can be highly undesirable when incorporated into a cosmetic product to which it can impart a grey tinge. Also, the relative insolubility of industrially produced melanins can prove detrimental in formulating useful products.

Where melanins produced industrially in the prior art are black, they may be bleached chemically to an acceptable brown colour. However, such bleaching steps are undesirable because they are costly, requiring difficult quality control, and use undesirably harsh chemicals, and the dark brown coloured material obtained is still too highly coloured.

The purpose of the present invention in one form is to provide melanins which can be lighter in colour than those produced industrially in the prior art and which can therefore be produced by a method which avoids the use of the undesirable bleaching step and also which are more compatible, eg. more soluble in, other ingredients used in cosmetic formulations incorporating such melanins.

According to the present invention in a first aspect there is provided a method of producing a melanin which comprises oxidising a phenolic compound at one or more hydroxyl groups thereof, wherein the phenolic compound is selected from compounds of formula (1) as follows and the oxidation is provided by biotransformation in the presence of an oxidoreductase enzyme; formula (1) is as follows:

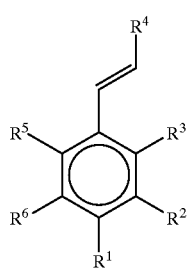

(1)

wherein
$R^1$ is H or OH
$R^2$ is H, OH or $OCH_3$
$R^3$ is H or OH
at least one of $R^1$ and $R^3$ being OH
$R^4$ is selected from H, R, —COOX and $R^7$—COOX, wherein R is an optionally substituted saturated or unsaturated alkyl group having from 1 to 12 carbon atoms, $R^7$ is an optionally substituted saturated or unsaturated alkylene group having from 1 to 12 carbon atoms and X is selected from H and aliphatic and aromatic ester forming groups; and
$R^5$ and $R^6$ is each independently selected from H, OH, $NH_2$, $OCH_3$, $CH_3$, SH, $NHCO_2$, $NHCH_3$, COOH and saturated or unsaturated alkyl groups having up to 8 carbon atoms.

The compound of formula (1) may conveniently be selected from 4-hydroxycinnamic acid and esters thereof formed by substitution at its acid moiety, caffeic acid and esters thereof formed by substitution at its acid moiety and ferulic acid and esters thereof formed by substitution at its acid moiety.

In formula (1) where $R^4$ is COOX or $R^7$—COOX, X may be the same as R as defined hereinbefore or $R^8$—O—$R^9$ where $R^8$ is selected from the same groups as $R^7$ and $R^9$ is selected from the same groups as R.

In formula (1) where $R^4$ is COOX or $R^7$—COOX, X may be a cyclic alkyl group optionally containing one or more substituents, especially hydroxyl groups. Quinic acid and its esters, eg. chlorogenic acid, and its esters, are especially preferred examples of this form.

In formula (1), where $R^4$ is COOX or $R^7$—COOX, X may alternatively be a group derived from 4-hydroxycinnamic acid (or a ring substituted derivative thereof) substituted in its (ring adjacent) hydroxy group.

Thus, the compounds of formula (1) may be esters of formula:

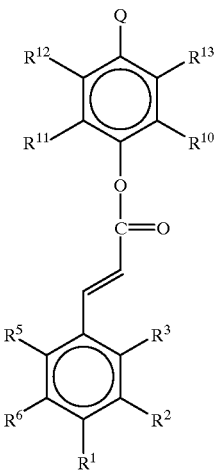

(2)

wherein $R^{10}$ is selected from H, OH and $OCH_3$; each of $R^{11}$, $R^{12}$, and $R^{13}$ is independently selected from H, OH, $NH_2$, $OCH_3$, $CH_3$, SH, $NHCO_2$, $NHCH_3$, COOH and $C_1$ to $C_8$ saturated or unsaturated alkyl groups; and Q is H, R, COOY or $R^{14}$—COOY, where $R^{14}$ is selected from the same groups as $R^7$ and Y is selected from the same groups as X.

Preferably, where $R^4$ or X or Y is R, R has six to ten carbon atoms. A particularly preferred example of R is octyl, especially 2-ethylhexyl.

Preferably, where X or Y is $R^8$—O—$R^9$ the total number of carbon atoms in the groups $R^8$ and $R^9$ is from two to six. A particularly preferred example of $R^8$—O—$R^9$ is —$C_2H_4$—O—$C_2H_5$.

Where the group $R^4$ includes a group $R^7$—COOX or where the group Q includes a group $R^{14}$—COOY the groups $R^7$ and $R^{14}$ preferably have from one to four carbon atoms. Particularly preferred examples of $R^7$ and $R^{14}$ are —$CH_2$—, —$C_2H_4$— and —CH=CH—.

In particular, the esters having the formulae:

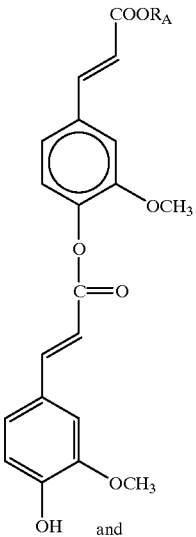 and (3)

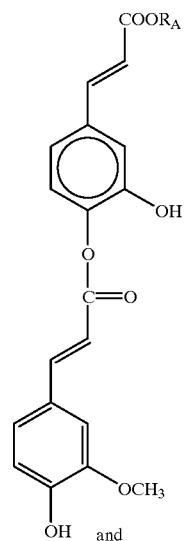 and (4)

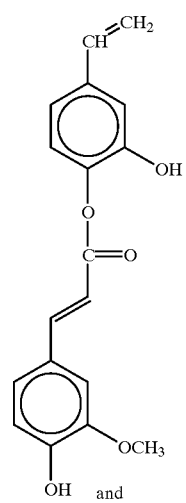 and (5)

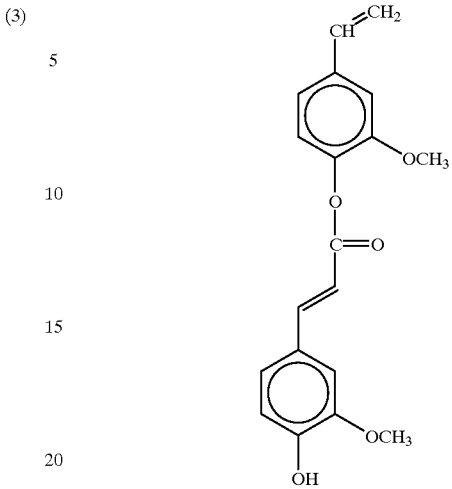

(6)

wherein $R_A$ represents 2-ethylhexyl and wherein $R_A$ represents $C_2H_4$—O—$C_2H_5$ are especially preferred.

The enzyme employed in the method according to the first aspect may be selected from the known group of oxidoreductase enzymes which act on oxygen as acceptor. For example, the enzyme may comprise a tyrosinase (0-diphenol oxidase, EC 1.10.3.1; EC 1.14.18.1) or a laccase (p-dipheroxidase EC 1.1.2). Oxygen is required to be present during the bioreaction in this case.

Alternatively, or in addition, the enzyme may be selected from the known group of oxidoreductase enzymes which act on peroxide as acceptor. For example, the enzyme may comprise a peroxidase (the group designated as EC 1.11.1, 1.11.2. etc). A peroxide, eg. hydrogen peroxide, is required to be present during the bioreaction in this case. The peroxidase may for example be a horseradish peroxidase, soy bean peroxidase or a microbial peroxidase.

The different enzyme systems (tyrosinase, laccase and peroxidase) react with their substrates to form intermediates and final products of different chemical structures. The tyrosinase and laccase enzymes oxidise phenols to form quinones which are highly reactive. The peroxidase enzyme oxidises the substrate by removing protons which leads to carbon-carbon bond formation between different substrate molecules.

According to the present invention in a second aspect there is provided a melanin produced by the method according to the first aspect.

We have found, surprisingly and beneficially, that melanins produced by the present invention have antioxidant activity (especially free radical quenching activity) and exhibit UV absorption as exemplified hereinafter. Furthermore, melanins produced from caffeic acid and derivatives thereof in accordance with the present invention are light brown and do not require bleaching as in the prior art. Also, melanins produced from ferulic acid and derivatives thereof are yellow, ie., lighter than those produced from caffeic acid and its derivatives. Additionally, melanins produced from 4-hydroxycinnamic acid and derivatives thereof can range from yellow to red/brown depending on the enzyme employed. Melanins derived from caffeic acid, ferulic acid and their derivatives are of the class known as allomelanins which do not contain sulphur or nitrogen.

Melanins produced from two or more of caffeic acid and derivatives thereof, ferulic acid and derivatives thereof and 4-hydroxycinnamic acid and derivatives thereof and optionally also 5-hydroxyindole and derivatives thereof may advantageously be mixed together to provide pigment formulations in which the darkness (or lightness) of the colouration of the pigment can be selected according to the relative amounts of the different types of melanin. Melanins produced from 5-hydroxyindole and derivatives thereof by enzyme transformation can be coloured from green to dark brown depending upon the enzyme employed.

Alternatively, melanins may be formed biochemically eg. using one or more of the above specified enzymes, from monomers comprising a mixture of caffeic acid and/or ferulic acid and/or 4-hydroxycinnamic acid or derivatives thereof eg. esters thereof and optionally 5-hydroxyindole or derivatives thereof, the composition of the mixture being selected according to pigment colouration required of the melanin product.

We have also found that the melanins produced in accordance with the present invention are generally more soluble in other ingredients conventionally used in the preparation of formulations for cosmetic and other applications than melanins made industrially in the prior art.

Furthermore, the melanins according to the second aspect of the present invention may be prepared under mild conditions using naturally occurring raw materials and enzymes.

For example, the synthesis of the melanins may be by natural processes that involve the use of enzymes, especially food plant derived enzymes and also natural raw materials especially those derived from food crop or plant sources. The compounds of formula (1) occur naturally, eg. in plant material and may be obtained as extracts therefrom or may be obtained by enzyme treatment of naturally occurring materials, eg. plant extracts.

For example ferulic acid compounds, ie. ferulic acid and derivatives thereof, may be prepared by a direct enzyme conversion of one or more compounds present in the plant cells. For example, wheat germ added to water may be treated by the enzyme preparations derived from microbial strains such as *Humicola insolens* that produce enzyme preparations containing ferulic acid esterase such as the enzyme Celluzyme™ (as described in a copending PCT patent application No. PCT/GB96/01345 by the present applicants) or Biofeed™ to produce ferulic acid directly. Alternatively, the ferulic acid compound may be prepared by enzyme conversion of one or more compounds present in plant cells to produce an intermediate such as caffeic acid or a derivative thereof followed by further treatment of the intermediate to produce the required ferulic acid compound. Preparation of caffeic acid compounds by enzyme treatment of compounds such as chlorogenic acid present in plant cells and tissues is described in our pending International Patent Application PCT/GB95/01324 and is further described on a further copending UK Patent Application of even date by the present applicants. The caffeic acid compound prepared thereby may be converted into the required ferulic acid compound by o-methylation of one of the hydroxyl groups of caffeic acid compound. This conversion step may be carried out chemically but is preferably carried out biochemically. For example, we have found that addition of the micro-organism *Streptomyces griseus* NRRL 8090 to caffeic acid compounds provides the required selective conversion.

Where one or more of the caffeic acid, ferulic acid or 4-hydroxycinnamic acid molecules is converted into a derivative thereof it may comprise one or more optional ring substituents. The substituents may be introduced into the ring of the ferulic acid molecule after the formation thereof. Alternatively, where the substituted ferulic acid compound is derived from a precursor such as caffeic acid, the precursor molecule may be substituted prior to conversion into the substituted ferulic acid compound.

Caffeic acid or ferulic acid or 4-hydroxycinnamic acid as appropriate may be processed by substitution of an electron donating group to one or more of the ortho and/or meta positions on the benzene ring of the core structure of the molecule. Examples of electron donating groups are OH, $NH_2$, $OCH_3$, $CH_3$, SH, $NHCO_2$, OCOH or a $C_1$ to $C_8$ saturated or unsaturated alkyl group. To produce such derivatives, the required ortho position may first be hydroxylated in a well known way, eg. according to the process of Ellis and Arheinn, *Phytochemistry*, 10,3069–3072 (1971) or Gestetner and Connee *Arch Biochem Biophys*, 163, 617–627(1974). The hydroxyl group may then be replaced with other electron donating groups by well-known methods, such as those disclosed in Vogels' *Textbook of Practical Organic Chemistry* by A. Vogel (Longman) or *Advanced Organic Chemistry Reaction Mechanisms and Structure*, 4th Edition by J. March (John Wiley & Sons). Alternatively, direct aromatic substitution can be carried out by known methods.

In the method of producing caffeic acid or ferulic acid the material to be treated by enzyme conversion preferably comprises a plant material which is added to water to form a slurry or semi-solid mass or moist cake. The water may be added to the plant material prior to adding the enzyme. Alternatively, the enzyme may be present in water when the enzyme and plant material are added to one another. The plant material may, for example, be in the form of a dry powder or pellet form and may be added to an aqueous solution of the enzyme.

The enzyme conversion may suitably be carried out in a bioreactor. The pH of the aqueous mixture of plant material and enzyme may suitably be monitored and held at or close to pH7, eg. in the range pH5 to pH9. Heating may be applied so that the bioreaction is carried out at an elevated temperature, e.g. in the range 35° C. to 55° C.

After the bioreaction has been completed the product formed may be extracted into a simple organic solvent such as ethyl acetate, isopropyl alcohol optionally with water, n-butanol, ethanol, hexanol, chloroform/methanol and the like and thereafter separated from the solvent e.g. in a known way eg. by drying over a drying agent such as sodium sulphate and/or by heating, preferably by evaporation of the solvent under vacuum.

Compounds of formula (1) which are esters of optionally substituted caffeic acid, ferulic acid and 4-hydroxycinnamic acid may be formed from these acids by well known procedures. For example the esterification reaction may be carried out biochemically eg. using a esterase/lipase enzyme. Alternatively, chemical conversion by a route well known to those skilled in the art, eg. dehydration by azeotropic water removal, physical or chemical water removal, or condensation via an activated intermediate such as an acid halide or activated ester may be used.

In a particular form of the method according to the first aspect the method may be carried out by applying to the body eg. skin or hair, of a human or animal a combination of ingredients eg. as separate constituent parts of a cosmetic formulation, whereby ferulic acid or a derivative thereof and/or caffeic acid or a derivative thereof and/or 4-hydroxycinnamic acid or a derivative thereof, optionally also with 5-hydroxyindole or a derivative thereof is contacted with the required enzyme added as part of the formulation ingredients to form the melanin in situ on the body.

Biotransformation of one or more compounds of formula (1) in this way optionally together with 5-hydroxyindole using an appropriate enzyme such as horse radish peroxidase and/or tyrosinase is particularly attractive for use in hair colourants since the melanin formed can have a suitable colour depending on the particular enzyme or combination of enzymes employed and can be prepared using less process steps than the prior art.

In the production of melanins by the method according to the first aspect we particularly prefer recovery of the melanin product from the peroxidase reactions by evaporative concentration (as exemplified hereinafter) in a known manner, eg. such as by rotary evaporation, falling film evaporation etc.

In the production of melanins by the method according to the first aspect, the consumption of starting material, eg. caffeic acid etc, may be monitored until the reaction is complete after which the reaction may be terminated in a known way. The precipitated melanin may be collected by a suitable separation technique, eg. centrifugation.

Where any of the melanins according to the second aspect of the present invention are to be used as cosmetic ingredients they may be made into cosmetic formulations by known methods using other ingredients which are well known in the cosmetics and personal care products field. For example, the formulation may be produced as a cream, ointment, lotion, emulsion, adhesive plaster. The other ingredients of the formulation may comprise ingredients selected from animal oils, plant oils, mineral oils, ester oils, waxes, higher alcohols, fatty acids, silicone oils, surfactants, phospholipids, alcohols, polyhydric alcohols water soluble polymers, clay and other inorganic pigment particles and water. Other known additives may include pH-adjusting agents, antioxidants, chelating agents, preservatives, biocides, colourants, perfumes, blood promoters, disinfectants, anti-inflammatory agents, cell activating agents, vitamins, amino-acids, moisture retaining agents and keratin-solubilising agents.

Embodiments of the present invention will now be described by way of example only with reference to the following examples (which are not intended to limit the scope of the invention in any way):

EXAMPLE 1

Production of a Caffeic Acid Derived Melanin by Tyrosinase

Caffeic acid (5 g) was dissolved in phosphate buffer (21, 100 mM, pH6.8) Tyrosinase (32 mg, 2400 units/mg, Sigma) was added and the solution equally divided between two 51 Erlenmeyer flasks. Reaction was incubated for 2 hours at 30° C., shaken at 200 rpm. Utilisation of caffeic acid was monitored by HPLC ($C_{18}$ column, 2 ml/min, water:acetonitrile (80:20)+acetic acid (1%), 290 nm). The reaction was terminated by addition of concentrated hydrochloric acid (500 ml) to the solution cooled on ice. A red/brown melanin precipitate was collected by centrifugation (4000 rpm, 15 min) The red/brown paste air dried. Yield: 3.35 g (65%).

EXAMPLE 2

Production of a Caffeic Acid/ferulic Acid Melanin by Tryosinase

Caffeic acid (500 mg) and ferulic acid (500 mg) were dissolved in ethanol (20 ml) plus phosphate buffer (200 ml, 100 mM, pH6.8) in a 500 ml Erlenmeyer flask. Tyrosinase (5 mg, 3900 units/mg, Sigma) was added and incubated for 2 hours at 30° C., shaken at 200 rpm. Utilisation of caffeic acid and ferulic acid was monitored by HPLC ($C_{18}$ column, 2 ml/min, water:acetonitirile (80:20)+acetic acid (1%), 290 nm). The reaction was terminated by addition of concentrated hydrochloric acid (10 ml) to the solution cooled on ice. A red/brown Melanin precipitate was collected by centrifugation (4000 rpm, 15 min). The red/brown paste was dried. Yield: 85.8 mg (8.58%).

EXAMPLE 3

Reaction of Ferulic Acid with Horse Radish Peroxidase Plus Hydrogen Peroxide

Ferulic acid (5 g) was dissolved in ethanol (100 ml) and citrate buffer (500 ml, 100 mM, pH 5.5) in a 1 l Erlenmeyer flask. Horseradish peroxidase (4 mg, Sigma) and hydrogen peroxide (22 ml, 27.5%) were added and the reaction was incubated for 4 hours at 30° C., shaken at 200 rpm. The reaction immediately formed a vivid yellow colour and was terminated by addition of hydrochloric acid (20 ml, 1.0 M). The yellow melanin precipitate formed was collected by filtration and air dried. Yield: 1.88 g (38%).

EXAMPLE 4

Production of a Caffeic Acid/ferulic Acid Melanin by Horse Radish Peroxidase Plus Hydrogen Peroxide Caffeic acid (500 mg) and ferulic acid (500 mg) were dissolved in ethanol (20 ml) plus citrate buffer (100 ml, 100 mM, pH5.5) in a 500 ml Erlenmeyer flask. Horseradish peroxidase (500 units, Sigmas) and hydrogen peroxidase (5 ml, 27.5%) were added and the solution incubated for 2 hours at 30° C., shaken at 200 rpm. Utilisation of caffeic acid and ferulic acid was monitored by HPLC (C18 column, 2 ml/min, water:acetonitirile (80:20)+acetic acid (1%), 290 nm). The reaction was terminated by addition of concentrated hydrochloric acid (10 ml) to the solution cooled on ice. A red/brown precipitate was collected by centrifugation (4000 rpm, 15 min) The red/brown paste was air dried. Yield: 126.3 mg (12.63%).

EXAMPLE 5

Production of a 5-Hydroxyindole Derived Melanin by Tyrosinase

5-Hydroxyindole (80 mg) was dissolved in methanol (0.25 ml) and water (4 ml, pH6.0) was added. Tyrosinase (5 mg, 2400 units/mg, Sigma) was added and the reaction was incubated for 2 hours at 37° C., shaken at 200 rpm. The reaction rapidly formed a bright red colouration followed by the formation of a black precipitate obtained in a good yield.

EXAMPLE 6

Production of a 5-Hydroxyindole Derived Melanin Using Horse Radish Peroxidase and Hydrogen Peroxide 5-Hydroxyindole (65 mg) was dissolved in methanol (0.15 ml) and citrate buffer (5.0 ml), pH 5.0, 100 mM) and hydrogen peroxide added. Horse radish peroxidase (0.1 mg, Sigma) was added and the reaction was incubated at 37° C., shaken at 200 rpm. The reaction rapidly formed a bright green colouration followed by the formation of a green precipitate obtained in good yield.

EXAMPLE 7

Production of a Chlorogenic Acid Derived Melanin by Tyrosinase

Chlorogenic acid (1 g) was dissolved in phosphate buffer (400 ml, 100 mM, pH6.8) and tyrosinase (6.4 mg, 2400 units/mg, Sigma) added. Reaction was incubated for 2 hours at 30° C., shaken at 200 rpm. Utilisation of chlorogenic acid was monitored by HPLC ($C_{18}$ column, 2 ml/min, water:acetonitirile (80:20)+acetic acid (1%), 290 nm). Reaction terminated by addition of concentrated hydrochloric acid (20 ml) to the solution cooled on ice and after 2 hours was then neutralised with aqueous sodium hydroxide (10.0 M). The product was recovered by evaporation at 50° C. under reduced pressure to yield a red/brown solid in good yield.

EXAMPLE 8

Production of a 4-Hydroxycinnamic Acid Derived Melanin by Tyrosinase

4-Hydroxycinnamic acid (2 mg) in ethanol (150 µl) was added to phosphate buffer (2 ml, 100 mM, pH6.8) and tyrosinase (0.1 mg in 5 µl phosphate buffer (100 mM, pH G.8) 3900 units/mg, Sigma) added. Reaction was incubated for 2 hours at 30° C., shaken at 200 rpm. During the incubation period a change in the colour of the reaction mixture was observed from colourless to red/brown indicating the formation of a melanin product by the enzyme.

EXAMPLE 9

Production of a 4-Hydroxycinnamic Acid Derived Melanin by Peroxidase and Hydrogen Peroxide 4-Hydroxycinnamic acid (2 mg) in ethanol (15 μl) was added to phosphate buffer (2 ml, 100 mM, pH6.8). Horseradish peroxidase (100 μl of 100 units per ml solution, Sigma) and hydrogen peroxide (100 μl, 27.5%) were added and the reaction was incubated for 2 hours at 30° C., shaken at 200 rpm. During the incubation period a change in the colour of the reaction mixture was observed from colourless to yellow indicating the formation of a melanin product by the enzyme.

EXAMPLE 10

Comparision of Peroxidases from Horse Radish, Soybean and Microbial Peroxides for the Reaction of Caffeic Acid with Hydrogen Peroxide The ability of the following peroxidases was assessed using 10 ml of a solution containing 2.5 mg/ml of caffeic acid citrate buffer (pH 5.5):
Horse radish peroxidase (Sigma Ltd, UK, P6782) 1200 Units;
Soybean peroxidase (Enzymol Ltd, USA) 68 units;
Microbial peroxidase (Noveozym 502, Novo Nordisk Ltd, Denmark) 200 μl;
Reaction was initiated by the addition of hydrogen peroxide (100 μl, 27.5%). In all three cases the reactions were observed to be identical, i.e. rapidly change from colourless to red/brown with no observable differences.

EXAMPLE 11

Production of a Caffeic Acid Derived Allomelanin by Tyrosinase Using Evaporation Caffeic acid (5 g) was dissolved in water (2 l) and adjusted to pH 7.0 using sodium hydroxide (5N). Tyrosinase (17 mg, 4400 units/mg, Sigma) was added and the solution equally divided between two 5 l Erlenmeyer flasks. Reaction was incubated overnight at 30° C. and shaken at 200 rpm. Product was recovered by evaporation at reduced pressure using a rotary evaporator and oven dried at 50° C. to yield a brown coloured powder. Yield: 5.5 g(100%).

EXAMPLE 12

Production of a Caffeic Acid Derived Allomelanin by Horse Radish Peroxidase+hydrogen Peroxide Caffeic acid (10 g) was dissolved in water (500 ml) in a 1 l Erlenmeyer flask and adjusted to pH6.5 using sodium hydroxide (5N). Horseradish peroxidase (8 mg, 2400 units/mg, Sigma) and hydrogen peroxide (44 ml, 27.5%) were added and the reaction was incubated overnight at 30° C., shaken at 200 rpm. The pH was monitored at pH6.5, catalase (4 mg, Sigma) was added to remove excess excess hydrogen peroxide and the reaction was incubated overnight at room temperature. Product was recovered by evaporation at reduced pressure using a rotary evaporator and oven dried at 50° C. to yield a brown coloured powder. Yield: 12.4 g(100%).

EXAMPLE 13

Assay of Antioxidant Activity of Melanin Products

Antioxidant activity of the melanin products was assessed using the DPPH free radical method as described by Brand-Williams et al. Lebensm-Weiss. u.Technol., 28, 25–30 (1995). The results are as in Table 1 as follows:

TABLE 1

| Source of Allomelanin | $EC_{50}$ (mg/L) | Rate × $10^6$ (mol DPPH/min/mg aox) |
|---|---|---|
| Caffeic Acid + Tyrosinase (Acid ppt) | 4 | 1.28 |
| Caffeic Acid + Ferulic acid + Peroxidase | 6.2 | 2.3 |
| Caffeic Acid + Peroxidase ($H_2O$ evap) | 3 | 6.5 |
| Ferulic acid + Peroxidase (Acid ppt) | 10.1 | 0.3 |
| Caffeic Acid + Ferulic Acid + Tyrosinase ($H_2O$ evap) | 5.4 | 1.4 |
| Caffeic Acid + Ferulic Acid + Tyrosinase ($H_2O$ evap) | 8 | 1.43 | wherein $EC_{50}$ (mg/L) Concentration required to reduce the concentration of DPPH by 50% under the defined experimental conditions.

Rate×$10^6$ (mol DPPH/ min/mg aox): Rate of DPPH consumed in assay per mg of antioxidant.

EXAMPLE 14

Absorbance Spectra of Melanin Products

Absorbance spectra (200 nm to 500 nm) were measured using 0.005% (w/v) solutions of the melanin products in either water (caffeic acid derived melanin utilising peroxidase and caffeic acid+ferulic acid derived melanin utilising peroxidase) or ethanol (caffeic acid derived melanin utlising tyrosinase) In all cases absorption was detected ove the complete range scanned, ie., 200 mn to 500 nm, which is indicative of melanin products. Absorption maxima are presented in Table 2 below.

TABLE 2

| Melanin Product + Enzyme Utilised | Absorption Maxima (nm) | Absorbance |
|---|---|---|
| Caffeic Acid + Tyrosinase | 310 | 905 |
| | 287 | 1,077 |
| Caffeic Acid + Peroxidase | 320 | 1,143 |
| | 285 | 1,345 |
| Caffeic Acid + Ferulic Acid + Peroxidase | 310 | 1,253 |
| | 285 | 1,406 |

What is claimed is:

1. A method of producing a melanin, which melanin is an allomelanin, the method comprising:

providing a phenolic compound, the compound having at least one hydroxyl group and having the following formula:

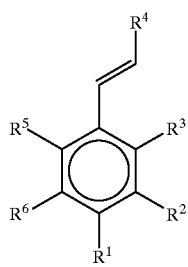

wherein $R^1$ and $R^3$ are selected from H and OH and at least one of $R^1$ and $R^3$ is OH;

$R^2$ is selected from H, OH, and $OCH_3$;

$R^4$ is selected from H, R, —COOX and $R^7$—COOX, wherein R is an alkyl group having from 1 to 12 carbon atoms, $R^7$ is an alkylene group having from 1 to 12 carbon atoms, and X is selected from H, an aliphatic ester-forming group, and an aromatic ester-forming group;

$R^5$ and $R^6$ are each independently selected from H, OH, $OCH_3$, $CH_3$, COOH and alkyl groups having up to 8 carbon atoms, and oxidizing the phenolic compound, wherein oxidation is by bioreaction in the presence of an oxidoreductase enzyme comprising a peroxidase.

2. A method as in claim 1, wherein the phenolic compound is selected from 4-hydroxycinnamic acid and esters thereof formed by substitution at its acid moiety, caffeic acid and esters thereof formed by substitution at its acid moiety, and ferulic acid and esters thereof formed by substitution at its acid moiety.

3. A method as in claim 1, wherein $R^4$ is selected from —COOX and $R^7$—COOX
wherein X is selected from R, as specified in claim 1, and
$R^8$—O—$R^9$,
where $R^8$ is selected from $R^7$, and
$R^9$ is selected from R.

4. A method as in claim 3 and wherein X is a linear or branched-chain alkyl group having from one to twelve carbon atoms or an ether group —$R^8$—O—$R^9$ having up to twelve carbon atoms in total.

5. A method as in claim 4 and wherein X is either $CH_2CH(C_2H_5)C_4H_9$ or $C_2H_4$—O—$C_2H_5$.

6. A method as in claim 1 wherein X is a cyclic alkyl group optionally containing one or more substituents.

7. A method as in claim 6 and wherein X is quinic acid or a derivative thereof.

8. A method as in claim 7 and wherein X is chlorogenic acid.

9. A method as in claim 1 wherein X is selected from a group derived from 4-hydroxycinnamic acid substituted in its ring adjacent its at least one hydroxyl group and a ring substituted derivative thereof.

10. A method as in claim 9 and wherein the phenolic compound is an ester of formula:

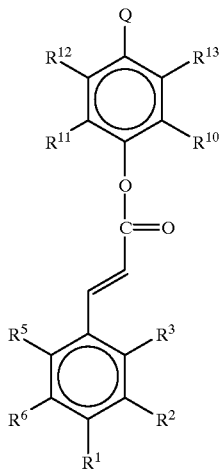

wherein $R^{10}$ is selected from H, OH or $OCH_3$, each of $R^{11}$, $R^{12}$ and $R^{13}$ is independently selected from H, OH, $OCH_3$, $CH_3$, COOH and $C_1$ to $C_8$ alkyl groups, and Q is H or COOY where Y is selected from the same groups as X as defined in claim 1.

11. A method as in claim 10 and wherein Y is the same as $R^8$—O—$R^9$ as defined in claim 4.

12. A method as in claim 11 and wherein Y is —$C_2H_4$—O—$C_2H_5$.

13. A method as in claim 10 and wherein the compound of formula (2) has the formula:

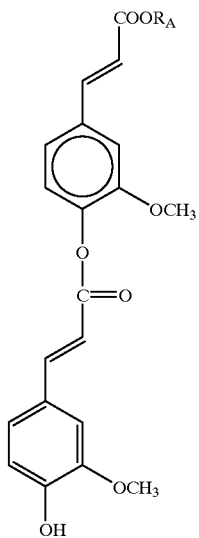

(3)

wherein $R_A$ is 2-ethylhexyl.

14. A method as in claim 10 and wherein the compound of formula (2) has the formula:

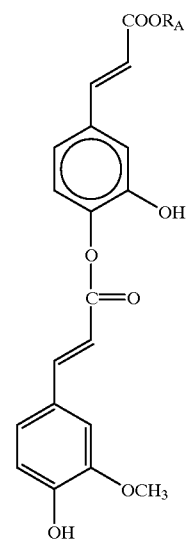

(4)

wherein $R_A$ represents $C_2H_4$—O—$C_2H_5$.

15. A method as in claim 10 and wherein the compound of formula (2) has the formula:

(5)

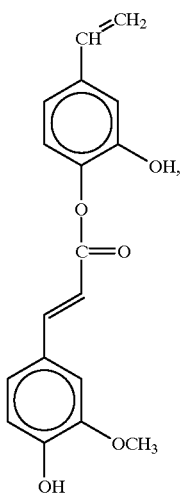

16. A method as in claim 10 and wherein the compound of formula (2) has the formula:

(6)

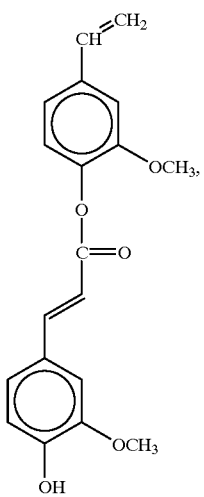

17. A method as in claim 10 and wherein Y is the same as R as defined in claim 1 and Y has from six to ten carbon atoms.

18. A method as in claim 17 and wherein Y is 2-ethylhexyl.

19. A method as in claim 1 and wherein the enzyme acts on oxygen as an acceptor and oxygen is present in the bioreaction.

20. A method according to claim 1 wherein the enzyme acts on peroxide as an acceptor and a peroxide is present in the bioreaction, the oxidizing occurring by action of the peroxidase in removing protons, the removing leading to different carbon-carbon bond formation.

21. A method according to claim 1 further comprising:
recovering a melanin product by evaporative concentration.

22. A method as in claim 1 wherein caffeic acid or a derivative thereof and/or ferulic acid or a derivative thereof and/or 4-hydroxycinnamic acid or a derivative thereof are bioreacted together.

23. A method as in claim 22 and wherein the caffeic acid or derivative thereof and/or ferulic acid or a derivative thereof is obtained from the enzyme treatment of plant material.

24. A melanin produced by a method as claimed in claim 1.

25. A colorant composition comprising a mixture of melanins as claimed in claim 24.

26. A cosmetic composition comprising:
a colorant composition according to claim 25.

27. A colorant composition as in claim 25 which shows increased solubility in water and/or cosmetic solvents and/or is less highly colored and/or retains good absorption in the uvA and uvB regions and/or shows good antioxidant activity.

28. A cosmetic composition comprising:
a melanin as claimed in claim 24.

29. A melanin as in claim 24 which shows increased solubility in water and/or cosmetic solvents and/or is less highly colored and/or retains good absorption in the uvA and uvB regions and/or shows good antioxidant activity.

30. A method according to claim 1 wherein, in oxidizing, the oxidizing occurs at the least one hydroxyl group.

31. A method according to claim 30 wherein, in oxidizing, the oxidizing occurs by removing protons leading to carbon-carbon bond formation between different molecules.

32. A method according to claim 1 wherein, in oxidizing, the oxidizing occurs by removing protons leading to carbon-carbon bond formation between different molecules.

\* \* \* \* \*